(12) United States Patent
Chen et al.

(10) Patent No.: US 6,683,199 B1
(45) Date of Patent: Jan. 27, 2004

(54) DICATIONIC NON-METALLOCENE GROUP 4 METAL COMPLEXES

(75) Inventors: Eugene Y. Chen, Fort Collins, CO (US); William J. Kruper, Jr., Sanford, MI (US)

(73) Assignee: Dow Global Technology Inc., Midland, MI (US)

( * ) Notice: Subject to any disclaimer, the term of this patent is extended or adjusted under 35 U.S.C. 154(b) by 4 days.

(21) Appl. No.: 10/088,279

(22) PCT Filed: Oct. 12, 2000

(86) PCT No.: PCT/US00/28278

§ 371 (c)(1),
(2), (4) Date: Mar. 15, 2002

(87) PCT Pub. No.: WO01/26806

PCT Pub. Date: Apr. 19, 2001

Related U.S. Application Data

(60) Provisional application No. 60/159,028, filed on Oct. 12, 1999.

(51) Int. Cl.[7] .......................... C07F 7/28; B01J 31/00; C08F 4/44

(52) U.S. Cl. ................. 556/27; 556/7; 556/9; 556/28; 502/152; 526/132; 526/134; 526/163

(58) Field of Search ........................... 556/9, 7, 27, 28; 502/152; 526/132, 134, 163

(56) References Cited

U.S. PATENT DOCUMENTS 5,726,115 A * 3/1998 Horton et al. .............. 502/152

* cited by examiner

*Primary Examiner*—Porfirio Nazario-Gonzalez

(57) ABSTRACT

Dicationic or partially dicationic Group 4 metal compounds having utility has addition polymerization catalysts among other uses and a method of preparation.

12 Claims, No Drawings

DICATIONIC NON-METALLOCENE GROUP 4 METAL COMPLEXES

This application claims benefit of priority from provisional application Ser. No. 60/159,028, filed Oct. 12, 1999.

BACKGROUND INFORMATION

The present invention relates to compounds that are useful, inter alia, as catalysts or catalyst components. More particularly, the present invention relates to dicationic compounds comprising a Group 4 metal atom (Ti, Zr, Hf) that are particularly adapted for use in the coordination polymerization of unsaturated compounds. Such compounds are particularly advantageous for use in a polymerization process wherein at least one polymerizable monomer is combined under polymerization conditions with a catalyst or catalyst composition to form a polymeric product.

It is previously known in the art to activate Ziegler-Natta polymerization catalysts, particularly such catalysts comprising Group 3–10 metal complexes containing delocalized π-bonded ligand groups, using Lewis acids to form catalytically active derivatives of such Group 3–10 metal complexes. Examples of suitable Lewis acids include tris(perfluorophenyl)borane and tris(perfluorobiphenyl)borane. Examples of such processes are disclosed in U.S. Pat. No. 5,721,185 and *J. Am. Chem. Soc.*, 118, 12451–12452 (1996), and elsewhere.

According to *J. Chem. Soc. Chem. Commun.*, 1999, 115–116, certain specifically substituted bis-Cp zirconocenedimethyl complexes may be converted to a dicationic derivative at −60° C. using multiple equivalents of trispentafluorophenylborane. The resulting metallocenes required the presence of either pendant phosphine moieties or benzyl groups on the cyclopentadienyl ring system and two equivalents of the methyltris(pentafluorophenyl)borate anion for charge balance. Upon heating even to −40° C. the product decomposed to give the corresponding monocationic complex and free tris(pentafluorophenyl)borane, thereby indicating the complexes would be unsuited for use as polymerization catalyst components.

In U.S. Pat. No. 5,318,935 metal complexes containing two amido groups optionally linked by means of a bridging group are disclosed.

Finally, in *Orpanometallics*, 1998, 17, 5908–5912, the reaction of the strongly Lewis acidic compound, tris(pentafluorophenyl)aluminum, with bis(cyclopentadienyl) zirconium dimethyl was shown to form an unstable (μ-methyl) derivative via methide abstraction, which rapidly collapsed through a back exchange reaction at temperatures above 0° C. to form bis(cyclopentadienyl) methylpentafluoro-phenyl zirconium. These compounds also would find little use as catalyst components for addition polymerizations due to the lack of temperature stability.

All of the foregoing attempts have failed to prepare a metal complex that is useful in catalytic applications, especially in the polymerization of one or more ethylenically unsaturated monomers under addition polymerization conditions.

SUMMARY OF THE INVENTION

According to the present invention there are now provided dicationic Group 4 metal compounds corresponding to the formula:

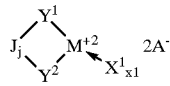

(I)

wherein:

$Y^1$ and $Y^2$ independently each occurrence is an anionic ligand group that is covalently bonded to M by means of a sigma bond through an oxygen, phosphorus or nitrogen atom, and containing up to 50 atoms, not counting hydrogen, said $Y^1$ and $Y^2$ optionally being joined through bridging group, J, and further optionally, $Y^1$ and $Y^2$ may also contain a coordinate/covalent bound to M;

J is an optional divalent bridging group having up to 20 atoms not counting hydrogen;

j is 0 or 1;

M is a Group 4 metal;

$X^1$ independently each occurrence is a Lewis base;

$x^1$ is 0, 1 or 2; and $A^-$ independently each occurrence is an anion of up to 50 atoms other than hydrogen, derived or derivable from a Lewis acid, said $A^-$ optionally forming an adduct with the metal complex by means of a μbridging group, and further optionally two $A^-$ groups may be joined together thereby forming a single dianion, optionally containing one or more μ-bridging groups.

The compounds of the invention may be formed by contacting a charge-neutral Group 4 metal coordination complex having two monovalent, anionic ligand groups, X (or optionally the two X groups together form a single divalent, anionic ligand group), or precursor(s) thereof (catalyst) with at least 2 molar equivalents of a charge-neutral, Lewis acid compound (activator), A, or a mixture thereof, such that the X groups of the Group 4 metal coordination complex are abstracted or partially abstracted, thereby forming a charge separated cation/anion pair, a zwitterionic metal complex, or a complex having both cation/anion and zwitteron functionality. Preferably the molar ratio of catalyst:activator employed in the foregoing process is from 1:2 to 1:10, more preferably the ratio is from 1:2 to 1:3, and most preferably from 1:2 to 1:2.5.

The foregoing process is illustrated by the following schematic drawing:

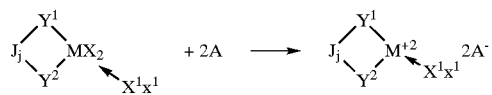

wherein $Y^1$, $Y^2$, M, J, j, X, $X^1$, $x^1$, A, and $A^-$, are as previously defined.

The present invented compounds are stable at elevated temperatures of at least 0° C., preferably at least 20° C. up to as high as 150° C. or higher and are usefully employed in a process for polymerization of ethylenically unsaturated monomers under solution, slurry, high pressure, or gas phase polymerization conditions. Relatively high molecular weight polymers may be readily obtained by use of the present metal complexes in the foregoing polymerization processes. Additionally, the foregoing metal complexes are suitably employed as initiators or catalysts for cationic polymerizations, such as the cationic polymerization of styrene or isobutylene, ring opening polymerizations, such as the polymerization of oxiranes or epoxides, especially propylene oxide, and the copolymerization of an olefin, especially ethylene, with a ring openable monomer.

Accordingly, the present invention additionally provides a process for the polymerization of one or more ethylenically unsaturated, addition polymerizable monomers comprising contacting the same, optionally in the presence of an inert aliphatic, alicyclic or aromatic hydrocarbon, under polymerization conditions with the above metal complex, or alternatively, forming the above metal complex in situ in the presence of or prior to addition to, a reaction mixture comprising one or more ethylenically unsaturated, polymerizable compounds.

DETAILED DESCRIPTION OF THE INVENTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. Where any reference is made herein to any publication, patent application or provisional patent application, the contents thereof are incorporated herein in its entirety by reference. By the term "Lewis acid", in reference to activator compounds herein, is meant compounds that are sufficiently electrophilic, such that a fully charge separated cation/anion pair, a $\mu$-bridged complex or a zwiterionic complex is formed upon combination of the respective catalyst and activators. Preferred anionic ligand groups, X, are hydrocarbyl, silyl, N,N-dialkylamido and alkanediylamido groups of up to 20 atoms not counting hydrogen, or two such X groups together are an alkanediyl or alkenediyl group which together with M form a metallocycloalkane or metallocycloalkene. By the term "partially dicationic" is meant that at least one $A^-$ group (or the entity formed from two $A^-$ groups collectively) is not fully charge separated from the metal center, M, or that at least one $A^-$ group (or the entity formed from two $A^-$ groups collectively) form a zwitterionic complex.

Preferred activators, A, are aluminum compounds containing at least one halohydrocarbyl ligand, preferably a fluoroaryl ligand. More preferred are tri(halohydrocarbyl) aluminum compounds having up to 50 atoms other than hydrogen, especially tri(fluoroaryl) aluminum compounds, most preferably tris(perfluoroaryl)aluminum compounds, and most highly preferably tris(pentafluorophenyl) aluminum. The activator compound may be used in pure form or in the form of an adduct with a Lewis base such as an ether.

Suitable Lewis acidic activators may be prepared by exchange between tris(pentafluorophenyl)boron and alkylaluminum- or alkyaluminumoxy- compounds such as alumoxanes or diisobutyl(2,6-di-t-butyl-4-methylphenoxy) aluminum, as disclosed in Biagini et. al., U.S. Pat. No. 5,602,269, and pending application U.S. Ser. No. 09/330673 (WO00/09515). The aluminum containing Lewis acids may be previously prepared and used in a relatively pure state or generated in situ by any of the foregoing techniques in the presence of the metal complex. Tris(perfluoroaryl)aluminum and exchange products obtained by mixing tris (perfluoroaryl)borane compounds, especially tris (pentafluoro-phenyl)boron, with methylalumoxane (MAO) or trialkylaluminum-, especially, triisobutylaluminum-modified methylalumoxane (MMAO) are highly preferred. This reaction product of tris(perfluoroaryl)boron with an alumoxane comprises a tris(fluoraryl)aluminum component of high Lewis acidity and a form of alumoxane which is rendered more Lewis acidic by the inherent removal of trimethylaluminum (TMA) via exchange to form trimethylborane. Optimized reaction products of these reactions correspond to the empirical formula:

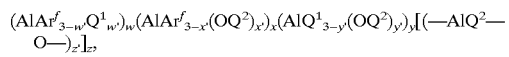

where;

$Ar^f$ is a fluorinated aromatic hydrocarbyl moiety of from 6 to 30 carbon atoms; preferably fluoroaryl, more preferably perfluoroaryl, and most preferably pentafluorophenyl;

$Q^1$ is $C_{1-20}$ alkyl, preferably methyl;

$Q^2$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^2$ groups may be covalently linked with each other to form one or more fused rings or ring systems;

w' is a number from 0 to 3;

w is a number from 0 to 1.0; preferably from 0.5 to 1.0, more preferably from 0.8 to 1.0;

x' is a number from 0 to 3;

x is a number from 1.0 to 0; preferably from 0.5 to 0, more preferably from 0.2 to 0;

y' is a number from 0 to 3;

y is a number from 1.0 to 0; preferably from 0.5 to 0, more preferably from 0.2 to 0;

z' is a number from 0 to 30; and z is a number from 0 to 20, preferably from 0 to 5, more preferably from 0 to 0.5.

The moieties, $(AlAr^f_{3-w'}Q^1_{w'})$, $(AlAr^f_{3-x'}(OQ^2)_{x'})$, $AlQ^1_{3-y'}(OQ^2)_{y'}$, and $[(-AlQ^2-O-)_{z'}]$, may exist as discrete entities or as dynamic exchange products. That is, the foregoing formula is an idealized representation of the composition, which may actually exist in equilibrium with additional exchange products.

An additional suitable Lewis acid activator may be formed in situ by reaction of residual or excess Lewis acid activator, preferably, tris(pentaflurophenyl)aluminum, with the anion resulting from initial abstraction of an X group from the metal complex. Accordingly, such anions resulting from the foregoing reaction are of the formula: $[A-\mu X-A]^-$, where, A- is the monovalent ligand derivative of A, preferably $-Al(C_6F_5)_3$, and $\mu X$ is the $\mu$-bridged derivative of X, preferably a $\mu$-methyl group. An example of such an anion is $[(C_6F_5)_3Al-\mu-CH_3-Al(C_6F_5)_3]^-$. However, because the group 4 metal complex and originally formed anion form a rather stable coordination pair under normal reaction conditions, the formation of the foregoing $\mu$-methyl bridged anion is likely observed only under reaction conditions that would favor destabilization of the previously disclosed coordination pair.

Additional examples of the anion $A^-$ are ligands of the formula: $[M^1Q_4]^-$, where $M^1$ is a Group 13 metal or metalloid, preferably Al, and Q independently each occurrence is an anionic ligand group, preferably an alkyl, aryl, aralkyl, or fluorinated aromatic ligand, that optionally may form a $\mu$-bridge to the metal, M. Most preferred examples of this type of $A^-$ anion are is $[CH_3Al(C_6F_5)_3]^-$ and $[\mu-CH_3Al(C_6F_5)_3]^-$.

Exemplary J groups include O, as well as groups corresponding to the formula:

(ER*$_2$)$_e$, (BNR*$_2$)$_e$, or PR*$_2$BR$^6{}_2$, wherein,

E independently each occurrence is C, Si, Sn, or Ge;

e=1,2,3, or 4;

R* independently each occurrence is $C_{1-10}$ hydrocarbyl, or optionally two R* groups are joined together; and R$^6$ independently each occurrence is halide, or $C_{1-12}$ hydrocarbyl.

Suitably, $Y^1$ and $Y^2$ are an amido group or phosphido group that is sigma bonded to M of the formula $=NR^1$, or $=PR^1$, where $R^1$ is hydrocarbyl, dihydrocarbylaminohydrocarbyl, silyl, silylhydrocarbyl, hydrocarbylsilyl, or a cyclic or polycyclic, nitrogen containing ring system having up to 20 atoms, not counting hydrogen, and optionally $R^1$ may be covalently or coordinately covalently bonded to J or M. Preferred sigma bonded ligand groups of the formula $=NR^1$ or $=PR^1$, are those wherein $R^1$ is alkyl or cycloalkyl of up to 10 carbons. Such complexes together with J form divalent bridging structures attached to the metal M.

Suitable compounds according to the present invention include compounds having the following structures:

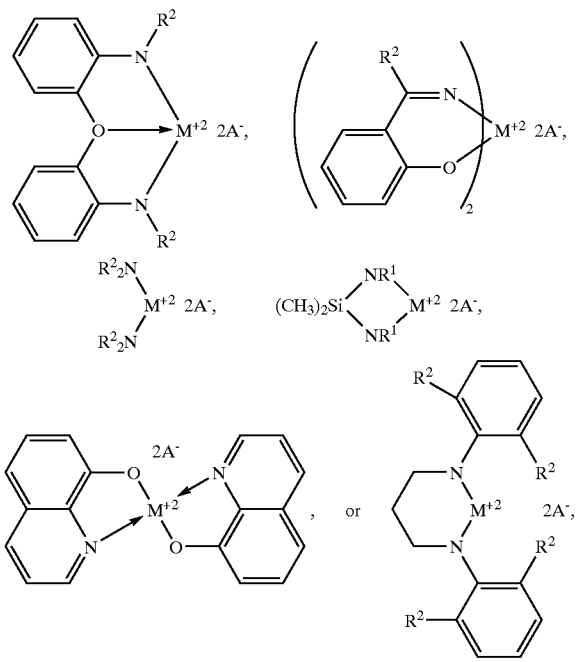

where M, $R^1$, and $A^-$ are as previously defined, and $R^2$, independently each occurrence is H or a hydrocarbyl, silyl, or trihydrocarbylsilyl-substituted hydrocarbyl group, said group having up to 20 atoms not counting hydrogen.

In the compounds of the invention, some or all of the bonds between M, $Y^1$ and $Y^2$ may possess partial bond characteristics. In addition, when $Y^1$ or $Y^2$ is a nitrogen containing, sigma bonded group, particularly a group of the formula, $=NR^1$, when $R^1$ is a primary alkyl group, an electronic interaction between the nitrogen and either one or both of the anionic moieties, $A^-$, may occur.

The process for preparing the dicationic complexes of the invention is conducted at temperatures from −80 to 220° C., preferably from 25 to 50° C., and preferably in a hydrocarbon diluent or solvent, especially $C_{4-12}$ aliphatic, cycloaliphatic or aromatic hydrocarbons or a mixture thereof.

Suitable addition polymerizable monomers for use with the foregoing novel catalyst compositions include ethylenically unsaturated monomers, acetylenic compounds, conjugated or non-conjugated dienes, and polyenes. Preferred monomers include olefins, for example alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, isobutylene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propylene, 1-butene, 1-pentene, 4-methyl-pentene-1,1-hexene, 1-octene, and combinations of ethylene and/or propene with one or more other alpha-olefins. Other preferred monomers include styrene, halo- or alkyl substituted styrenes, vinylbenzocyclobutene, 1,4-hexadiene, dicyclopentadiene, ethylidene norbornene, and 1,7-octadiene. Mixtures of the above-mentioned monomers may also be employed.

In general, the polymerization may be accomplished under conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres (100 kPa to 300 Pma).

Preferred processing conditions include solution polymerization, more preferably continuous solution polymerization processes, conducted in the presence of an aliphatic or alicyclic liquid diluent. By the term "continuous polymerization" is meant that at least the products of the polymerization are continuously removed from the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, 1-butene, isobutylene, butadiene, 1-pentene, cyclopentene, 1-hexene, cyclohexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators of the present invention.

In most polymerization reactions the molar ratio of catalyst:polymerizable compounds employed is from $10^{-12}$:1 to $10^{-1}$:1, more preferably from $10^{-12}$:1 to $10^{-5}$:1.

Molecular weight control agents may be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution α-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed in the gas phase polymerization and copolymerization of olefins, preferably by supporting the catalyst composition by any suitable technique. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type that employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid or can be condensed to provide such a liquid, this can be suitably fed to the bed to provide an evaporative cooling effect. Examples of olefin monomers which can be employed in this manner are olefins containing from about 3 to about eight, preferably from 3 to six carbon atoms. The volatile liquid evaporates in the hot fluidized bed to form gas which mixes with the fluidizing gas. If the volatile liquid is a monomer or comonomer, it may undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749. A particularly preferred method of recycling the liquid to the bed is to separate the liquid from the recycle gas stream and to reinject this liquid directly into the bed, preferably using a method that generates fine droplets of the liquid within the bed. This type of process is described in WO 94/28032.

The polymerization reaction occurring in the gas fluidized bed is catalyzed by the continuous or semi-continuous addition of catalyst. Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerzation of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with a dry inert gas such as nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

EXAMPLES

It is understood that the present invention is operable in the absence of any component that has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc. The $^1$H (300 MHz) and $^{13}$C NMR (75 MHz) spectra were recorded on a Varian XL-300 spectrometer. The $^1$H and $^{13}$C NMR spectra are referenced to the residual solvent peaks and are reported in ppm relative to tetramethylsilane. All J values are given in Hz. Tetrahydrofuran (THF), diethylether, toluene, and hexane were used following passage through double columns charged with activated alumina and Q-5® catalyst (available from Englehardt Chemicals, Inc.). The compounds $BCl_3$-$SMe_2$, $B(NMe_2)_3$, n-BuLi, Bis(catecholato)diboron, $LiNMe_2$ and 2,6-diisopropylaniline were all used as purchased from Aldrich. All syntheses were performed under dry nitrogen or argon atmospheres using a combination of glove box and high vacuum techniques.

Examples 1–2
Preparation of Metal Complex
A. (N,N'-di(2,6-diisopropylphenyl)-1,3-propanediamido) titanium Dimethyl (DIP, Ex. 1 and Comp. A)

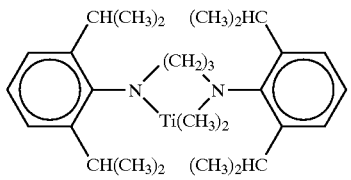

This compound was prepared substantially according to the teachings of U.S. Pat. No. 5,318,935.

B. bis(N,N'-di(2,6-diisopropylphenyl)amido) (dimethylamino)boron)titanium Dimethyl (BAB, Ex. 2)

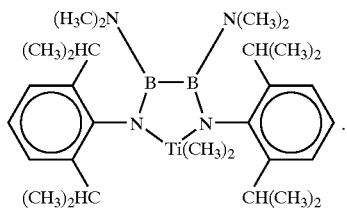

Preparation of Chlorobis(dimethylamido)borane $BCl_3SMe_2$ (62.000 g, 345.78 mmol) and $B(NMe_2)_3$ (98.921 g, 691.56 mmol) were stirred together at room temperature overnight under a nitrogen bubbler. The mixture was then heated to reflux for one hour to drive off any residual $SMe_2$. Allowing the pale yellow liquid to stir to room temperature followed by filtration resulted in the isolation of the desired product (139.436 g, 93.3 percent yield).

$^1$H NMR ($C_6D_6$): δ2.49 (s, 12 H). $^{13}$C NMR ($C_6D_6$) δ39.86.

Preparation of Tetrakis(dimethylamido)diborane via ClB(NMe)$_2$

Chlorobis(dimethylamido)borane (30.000 g, 223.19 mmol) was refluxed in hexane (200 mL) as Na/K alloy [Na (1.539 g, 66.96 mmol)/8.726 g K (8.726 g, 223.19 mmol)] was added dropwise to the solution. After the first several drops the reaction initiated as evidenced by a sudden increase in the reflux. The heat was then turned off and the alloy added slowly so as to maintain a reflux. After the addition was complete, the reaction mixture was heated to reflux for an additional hour and then stirred at room temperature for three hours. The mixture was then filtered through a diatomaceous earth filter pad and the volatile components removed, resulting in the isolation of a yellow liquid. Fractional vacuum distillation resulted in the isolation of the desired compound as a pale yellow liquid (7.756 g, 35.1 percent yield).

$^1$H NMR ($C_6D_6$): δ2.73 (s, 24 H). $^{13}$C NMR ($C_6D_6$) :δ41.37.

Preparation of Tetrakis(dimethylamido)diborane via Bis(catecholato)-diboron

Lithium dimethylamide (10.70 g, 210.0 mmol) was added slowly as a solid to a solution of bis(catechoiato)diboron (10.00 g, 42.00 mmol) in diethylether (200 mL) at −20° C. This mixture was then allowed to stir for an additional 40 hours at room temperature. After the reaction period, the ether was removed under vacuum and the residue extracted and filtered using hexane. Removal of hexane resulted in the isolation of a yellow oil. Fractional vacuum distillation resulted in the isolation of the desired compound as a pale yellow liquid (5.493 g, 66.0 percent yield).

Preparation of Bis(dimethylamido)diborondichloride

Tetrakis(dimethylamido)diborane (7.756 g, 39.19 mmol) was stirred in diethylether (100 mL) at −78° C. as HCl (156.75 mmol, 156.75 mL of 1.0 M solution in diethylether) was added dropwise. This mixture was then allowed to stir for six hours at room temperature. After the reaction period the volatiles were removed and the residue extracted and filtered using hexane. Removal of the hexane resulted in the isolation of a yellow oil. Fractional vacuum distillation resulted in the isolation of the desired compound as a pale yellow liquid (4.722 g, 66.7 percent yield).

$^1$H NMR ($C_6D_6$):δ2.40 (s, 6 H), 2.50 (s, 6 H). $^{13}$C NMR ($C_6D_6$): δ37.62, 41.78.

Preparation of 2,6-Diisopropylaniline, Lithium Salt n-BuLi (56.40 mmol, 35.25 mL of 1.6 M solution in hexane) was added dropwise to a solution of 2,6-diisopropylaniline (10.00 g, 56.40 mmol) in hexane (100 mL). This mixture was allowed to stir for 3 hours during which time a white precipitate formed. After the reaction period the mixture was filtered and the white salt washed with hexane and dried under vacuum and used without further purification or analysis (9.988 g, 96.7 percent yield).

Preparation of 1,2-Bis(2,6-diisopropylanilide)-1,2-bis(dimethylamido)-diborane

Bis(dimethylamido)diborondichloride (2.350 g, 13.00 mmol) in diethylether (10 mL) was added dropwise to a solution of 2,6-diisopropylaniline, lithium salt (4.765 g, 26.01 mmol) in diethylether (50 mL) at 0° C. This mixture was then allowed to stir overnight at room temperature. After the reaction period the volatiles were removed and the residue extracted and filtered using hexane. Removal of the hexane resulted in the isolation of a the desired product as a white solid (5.322 g, 88.9 percent yield).

$^1$H NMR (toluene-$d_8$):δ0.9–1.4 (br m, 24 H), 2.3 (s, 6 H), 2.8 (s, 6 H), 3.7 (s, 2 H), 7.0 (br s, 6 H).

$^{13}$C NMR (toluene-$d_8$): δ22.51, 24.03 (br), 28.17, 36.82, 42.67, 123.19, 124.78, 140.71, 145.02 (br).

MS(EI): m/z 460.4025 (M−H)$^+$, calcd. (M−H)$^+$ 460.4026.

Preparation of 1,2-Bis(2,6-diisopropylanilide)1,2-bis(dimethylamido)diborane, Dilithium Salt 1,2-Bis(2,6-diisopropylanilide)-1,2-bis(dimethylamido) diborane (1.820 g, 3.950 mmol) was stirred in hexane (75 mL) as n-BuLi (7.91 mmol, 4.94 mL of 1.6 M solution in hexane) was added dropwise. This mixture was then allowed to stir overnight. After the reaction period the mixture was filtered and the salt washed well with hexane and dried under vacuum resulting in the isolation of the desired product as a white powder (1.6878 g, 90.4 percent yield).

$^1$H NMR (THF-$d_8$): δ1.04 (d, 6 H), 1.18 (d, 6 H), 2.45 (s, 12 H), 3.66 (septet, 4 H), 6.29 (t, 2 H), 6.73 (d, 4 H).

$^{13}$C NMR (THF-$d_8$): δ24.88, 25.34, 28.00, 40.91, 114.40, 121.95, 137.21, 158.76.

Anal. Calcd. For $C_{28}H_{46}N_4B_2Li_2$: C, 70.92; H, 9.78; N, 11.81. Found: C, 70.90; H, 11.12; N, 9.66.

Preparation of Dichloro-[1,2-Bis(2,6diisopropylanilide)-1,2-bis(dimethylamido)diborane]titanium 1,2-Bis(2,6-diisopropylanilide)-1,2-bis(dimethylamido) diborane, dilithium salt (0.600 g, 1.27 mmol) in THF (20 mL) was added dropwise to a slurry of $TiCl_3(THF)_3$(0.471 g, 1.27 mmol) in THF (50 mL) at 0° C. This mixture was then allowed to stir at room temperature for 45 minutes. $PbCl_2$(0.177 g, 0.640 mmol) was then added as a solid and the mixture allowed to stir for an additional 30 minutes. After the reaction period the volatiles were removed and the residue extracted and filtered using hexane. Concentration of the hexane and cooling to −10° C. overnight resulted in the formation of orange X-ray quality crystals (0.156 g, 21.3 percent yield).

$^1$H NMR (toluene-d$_8$): δ1.23 (d, 6 H), 1.45 (d, 6 H), 2.17 (s, 6 H), 2.76 (s, 6 H), 3.5 (septet, 4 H), 7.11 (s, 6 H).

$^{13}$C NMR (toluene-d$_8$): δ24.94, 24.67, 29.48, 39.33, 42.93, 124.08 (br), 17.23, 150.64.

MS(EI): m/z 578.2789 (M)$^+$, calcd. (M)$^+$ 578.2781.

Anal. Calcd. For C$_{28}$H$_{46}$B$_2$N$_2$TiCl$_2$: C, 58.07; H, 8.01; N, 9.67. Found: C, 58.28; H, 8.20; N, 9.42.

Preparation of Dimethyl-[1,2-Bis(2,6diisopropylanilide)-1,2-bis(dimethylamido)diborane]titanium Dichloro-[1,2-Bis(2,6-diisopropylanilide)-1,2-bis(dimethylamido)diborane]titanium (0.272 g, 0.470 mmol) was stirred in diethylether (40 mL) as MeMgBr (0.940 mmol, 0.313 mL of 3.0 M solution in diethylether) was added dropwise. This mixture was allowed to stir for one hour. After the reaction period the volatiles were removed and the residue extracted and filtered using hexane. Removal of the hexane resulted in the isolation of the desired product as a dark yellow oil (0.209 g, 82.5 percent yield).

$^1$H NMR (C$_6$D$_6$): δ1.05 (s, 6 H), 1.21 (d, $^3J_{HH}$=6.9 Hz, 16 H), 1.32 (d, $^3J_{HH}$=6.3 Hz, 16 H), 2.19 (s, 6 H), 2.69 (s, 6 H), 3.58 (br, 2 H), 7.0–7.2 (m, 6 H).

$^{13}$C NMR (C$_6$D$_6$): δ24.06, 24.83, 29.31, 39.58, 42.93, 57.38, 123.97, 125.18, 139.5 (br), 149.45.

MS(EI): m/z 538.3858 (M)$^+$, calcd. (M)$^+$ 538.3793.

Solution Polyethylene Polymerization

Mixed hexanes and 1-octene were purified by sparging with purified nitrogen followed by passage through columns containing alumina (A-2, available from LaRoche Inc.) and Q5 reactant (available from Englehard Chemicals Inc.) at 50 psig (340 kPa) using a purified nitrogen pad. All transfers of solvents and solutions described below were accomplished using a gaseous pad of dry, purified nitrogen or argon. Gaseous feeds to the reactor were purified by passage through columns of A-204 alumina (available from LaRoche Inc.) and Q5 reactant. The aluminas were previously activated by treatment at 375° C. with nitrogen and Q5 reactant was activated by treatment at 200° C. with 5 percent hydrogen in nitrogen.

Batch reactor polymerizations were conducted in a two liter Parr reactor equipped with an electrical heating jacket, internal serpentine coil for cooling, and a bottom drain valve. Pressures, temperatures and block valves were computer monitored and controlled. Mixed alkanes solvent (about 740 g) and 1-octene (118 g) were measured in a solvent shot tank fitted with a differential pressure transducer or weigh cell. These liquids were then added to the reactor from the solvent shot tank. The contents of the reactor were stirred at 1200 rpm. Hydrogen was added by differential expansion (Δ25 psi, 170 kPa) from a 75 ml shot tank initially at 300 psig (2.1 Mpa). The contents of the reactor was then heated to the desired run temperature under 500 psig (3.4 Mpa) of ethylene pressure. The catalyst composition (as a 0.0050 M solution in toluene) and cocatalyst (tris(pentafluorophenyl)aluminum, FAAL) were combined in the desired ratio in the glove box and transferred from the glove box to the catalyst shot tank through 1/16 in (0.16 cm) tubing using toluene to aid in the transfer. The catalyst tank was then pressurized to 700 psig (4.8 Mpa) using nitrogen. After the contents of the reactor had stabilized at the desired run temperature of 140° C., the catalyst was injected into the reactor via a dip tube. The temperature was maintained by allowing cold ethylene glycol to pass through the internal cooling coils. The reaction was allowed to proceed for 15 minutes with ethylene provided on demand. The contents of the reactor were expelled into a 4 liter nitrogen purged vessel and quenched with isopropyl alcohol. Approximately 10 ml of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation) were added. Volatile materials were removed from the polymers in a vacuum oven that gradually heated the polymer to 140° C. overnight and cooled to at least 50° C. prior to removal from the oven. After completion of the polymerization, the reactor was washed with 1200 ml of mixed hexanes solvent at 150° C. before reuse. Results are contained in Table 1.

TABLE 1

| Ex. | Catalyst | cocatalyst | Catalyst/cocatalyst (μmoles) | Efficiency (g/mg Ti) | Density g/ml | melt index** (dg/min) |
|---|---|---|---|---|---|---|
| A* | DIP | FAAL | 5/5 | 1 | — | — |
| 1 | DIP | FAAL | 5/20 | 34 | 0.915 | 2.0 |
| 2 | BAB | FAAL | 5/20 | 40 | 0.896 | >500 |

*Comparative, no bimetallic anion formed due to 1:1 molar ratio of catalyst and cocatalyst
**determined by micromelt index technique As may be seen by reference to Table 1, a complex formed by use of at least 2 equivalents of cocatalyst gave a catalyst species having substantially greater activity as evidenced by catalyst efficiency than the catalyst species formed from use of only a 1:1 molar ratio of catalyst and cocatalyst.

What is claimed is:

1. A dicationic Group 4 metal compound corresponding to the formula:

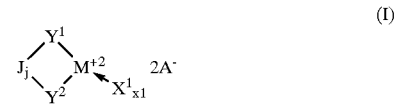

(I)

wherein:

Y$^1$ and Y$^2$ independently each occurrence is an anionic ligand group that is covalently bonded to M by means of a sigma bond through a nitrogen atom, and containing up to 50 atoms, not counting hydrogen, said Y$^1$ and Y$^2$ being joined through bridging group, J, and optionally, Y$^1$ and Y$^2$ may also contain a coordinate/covalent bound to M;

J is a divalent bridging group having up to 20 atoms not counting hydrogen;

j is 1;

M is a Group 4 metal;

X$^1$ independently each occurrence is a Lewis base;

x$^1$ is 0, 1 or 2; and

A$^−$ independently each occurrence is an anion of up to 50 atoms other than hydrogen, derived or derivable from a Lewis acid, said A$^−$ optionally forming an adduct with the metal complex by means of a μ-bridging group, and further optionally two A$^−$ groups may be joined together thereby forming a single dianion, optionally containing one or more μ-bridging groups.

2. A compound according to claim 1 corresponding to the formula:

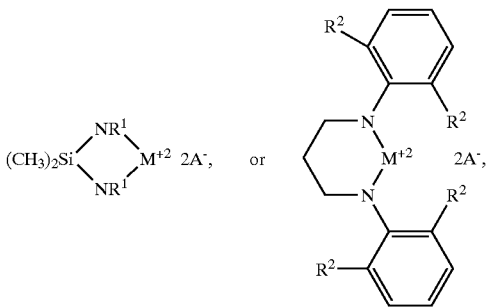

where M, and A⁻ are as previously defined in claim 1,
$R^1$ is hydrocarbyl, dihydrocarbylaminohydrocarbyl, silyl, silylhydrocarbyl, hydrocarbylsilyl, or a cyclic or polycyclic, nitrogen containing ring system having up to 20 atoms, not counting hydrogen, and optionally $R^1$ may be covalently or coordinately covalently bonded to J or M, and $R^2$, independently each occurrence, is H or a hydrocarbyl, silyl, or trihydrocarbylsilyl-substituted hydrocarbyl group, said group having up to 20 atoms not counting hydrogen.

3. A compound according to claim 1 wherein A⁻ is $[CH_3Al(C_6F_5)_3]^-$ or $[\mu\text{-}CH_3Al(C_6F_5)_3]^-$.

4. A process for preparing a dicationic Group 4 metal compound according to claim 1 comprising contacting a charge-neutral Group 4 metal coordination complex having two Lewis basic anionic ligand groups, X, or precursor(s) thereof corresponding to the formula:

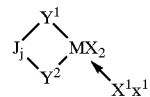

wherein, J, j, $Y^1$, $Y^2$, M, $X^1$ and $x^1$ are as defined in claim 1, with at least 2 molar equivalents of a charge-neutral, Lewis acidic compound, A, such that at least two of the Lewis basic groups of the Group 4 metal coordination complex are abstracted or partially abstracted, thereby forming a charge separated cation/anion pair, a zwitterionic metal complex, or a complex having both cation/anion and zwitterion functionality.

5. A compound according to claim 1 wherein J is $(ER^*_2)_e$, $(BNR^*_2)_e$, or $PR^*_2BR^6_2$, wherein, E independently each occurrence is C, Si, Sn, or Ge;

e=1, 2, 3, or 4;

R* independently each occurrence is $C_{1-10}$ hydrocarbyl, or optionally two R* groups are joined together; and $R^6$ independently each occurrence is halide, or $C_{1-12}$ hydrocarbyl.

6. A compound according to claim 1 wherein J is $(BNR^*_2)_e$, wherein, e=1, 2, 3, or 4; and R* independently each occurrence is $C_{1-10}$ hydrocarbyl, or optionally two R* groups are joined together.

7. A compound according to claim 6 which is the dicationic derivative of dimethyl-[1,2-bis(2,6-diisopropylanilide)-1,2-bis(dimethylamido)diborane] titanium.

8. A compound according to claim 6 formed by reaction of dimethyl-[1,2-bis(2,6-diisopropylanilide)-1,2-bis(dimethylamido)diborane]titanium with tris(pentafluorophenyl)aluminum.

9. The process of claim 4 wherein the charge-neutral Group 4 metal compound is dimethyl-[1,2-bis(2,6-diisopropylanilide)-1,2-bis(dimethylamido)-diborane] titanium.

10. The process of claim 4 wherein the charge neutral, Lewis acidic compound is tris(pentafluorophenyl)aluminum.

11. The process of claim 9 wherein the charge neutral, Lewis acidic compound is tris(pentafluorophenyl) aluminum.

12. In a process for the polymerization of one or more olefin monomers to form a high molecular weight polymer comprising contacting said one or more olefin monomers with a catalyst under olefin polymerization conditions, the improvement wherein the catalyst comprises the compound of any one of claims 1–3 or 5–8 or the compound preparable by any of claim 4, 9, 10 or 11.

* * * * *